US006242587B1

(12) United States Patent
Naik et al.

(10) Patent No.: US 6,242,587 B1
(45) Date of Patent: Jun. 5, 2001

(54) DNA MOLECULES ENCODING A CALCIUM-INTEGRIN BINDING PROTEIN

(75) Inventors: Uhlas P. Naik, Carroboro; Leslie V. Parise, Chapel Hill, both of NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 08/720,625

(22) Filed: Oct. 2, 1996

(51) Int. Cl.$^7$ .......................... C07H 21/04; C12N 15/12; C12N 15/00; C12N 15/63
(52) U.S. Cl. .................. 536/23.5; 435/252.3; 435/320.1; 435/455; 435/471; 435/476; 530/350; 536/23.1
(58) Field of Search .................................. 536/23.1, 23.5; 435/172.3, 320.1, 252.3, 440, 471; 530/350

(56) References Cited

U.S. PATENT DOCUMENTS

| 5,344,783 | 9/1994 | Scarborough et al. . |
| 5,380,646 | 1/1995 | Knight et al. . |
| 5,492,890 | 2/1996 | Ginsberg et al. . |
| 5,523,209 | 6/1996 | Ginsberg et al. . |
| 5,529,902 | 6/1996 | Kottke et al. . |

OTHER PUBLICATIONS

1. Naik et al. J Biol Chem. 272:4651–4654 (1997).*
Alberts et al. (Eds)., The Molecular Biology of the Cell, 3d ed., Garland Publishing Inc., New York, 1994 p. 996–1000.
Leung–Hagesteijn et al., "Cell attachment to extracellular matrix substrates is inhibited upon downregulation of expression of calreticulin, an intracellular integrin α–subunit–binding protein", *Journal of Cell Science*, 107, pp. 589–600 (1994).

Crabtree and Clipstone, "Signal Transmission Between The Plasma Membrane And Nucleus Of T Lymphocytes", *Annu. Rev. Biochem.*, 63: 1045–83 (1994).

Wera and Hemmings, "Serine/threonine protein phosphatases", *Biochem J.*, 311: 17 (1995), p. 17–29.

Shattil et al., "$\beta_3$–Endonexin, A Novel Polypeptide That Interacts Specifically with the Cytoplasmic Tail of the Integrin $\beta_3$ Subunit", *J. Cell Biol.*, 131:807 (1995), p. 807–816.

Naik et al., (Abstract 246) "Integrins and Signalling Events in Cell Biology and Disease", Keystone Symposia, Molecular & Cellular Biology, Keystone, Colorado, (Jan. 1996); p. 54.

Hannigan et al., "Regulation of cell adhesion and anchorage–dependent growth by a new $\beta_1$–integrin–linked protein kinase", *Nature*, 379: 91 (1996).

Barroso et al., "A Novel $Ca^{2+}$–binding Protein, p22, Is Required for Constitutive Membrane Traffic", *J. Biol. Chem.*, 271: 17, 10183–10187 (1996).

Barreuther et al., "The Role of Phosphorylation in Modulating $\beta_1$ Integrin Localization", *Experimental Cell Research*, 222, pp. 10–15 (1996).

Wei et al., "Regulation of Integrin Function by the Urokinase Receptor", *Science*, 273, pp. 1551–1555 (1996).

* cited by examiner

Primary Examiner—Phillip Gambel
(74) Attorney, Agent, or Firm—Myers Bigel Sibley & Sajovec

(57) ABSTRACT

A $Ca^{2+}$-binding protein that interacts specifically with the integrin αIIb subunit cytoplasmic domain is described. This protein is expressed in platelets and interacts with the fibrinogen receptor, integrin αIIbβ3.

4 Claims, 6 Drawing Sheets

```
TCTGCGTCTCGAGGCGAGTTGGCGGAGCTGTGCGCGCGGCGGGGCGATGGGGGGCTCGGG  60
                                                   M G  G S G   5
CAGTCGCCTGTCCAAGGAGCTGCTGGCCGAGTACCAGGACTTGACGTTCCTGACGAAGCA 120
  S R L S K E L L A E Y Q D L T F L  I  K Q                   25
GGAGATCCTCCTAGCCCACAGGCGGTTTTGTGAGCTGCTTCCCCAGGAGCAGCGGAGCGT 180
  E I L L A H R R F C E L L P Q E Q R S V                     45
GGAGTCGTCACTTCGGGCACAAGTGCCCTTCGAGCAGATTCTCAGCCTTCCAGAGCTCAA 240
  E S  S  L R A Q V P F E Q I L  S  L P E L K                 65
GGCCAACCCCTTCAAGGAGCGAATCTGCAGGGTCTTCTCCACATCCCCAGCCAAAGACAG 300
  A N P F K E R I C R V F S T S P A K D S                     85
CCTTAGCTTTGAGGACTTCCTGGATCTCCTCAGTGTGTTCAGTGACACAGCCACGCCAGA 360
  L  S  F E D F L D L L S V F S D T A T P D                  105
CATCAAGTCCCATTATGCCTTCCGCATCTTTGACTTTGATGATGACGGAACCTTGAACAG 420
  I K S H Y A F R I F  D F D D D G T L N R                   125
AGAAGACCTGAGCCGGCTGGTGAACTGCCTCACGGGAGAGGGCGAGGACACACGGCTTAG 480
  E D L  S R L V N C L T G E G E D T R L  S                  145
TGCGTCTGAGATGAAGCAGCTCATCGACAACATCCTGGAGGAGTCTGACATTGACAGGGA 540
  A S E M K Q L I D N I L E E  S  D I D R D                  165
TGGAACCATCAACCTCTCTGAGTTCCAGCACGTCATCTCCCGTTCTCCAGACTTTGCCAG 600
  G T I N L S E F  Q H V I S R S P D F A S                   185
CTCCTTTAAGATTGTCCTGTGACAGCAGCCCCAGCGTGTGTCCTGGCACCCTGTCCAAGA 660
  S  F K I V L *
ACCTTTCTACTGCTGAGCTGTGGCCAAGGTCAAGCCTGTGTTGCCAGTGCGGGCCAAGCT 720
GGCCCAGCCTGGAGCTGGCGCTGTGCAGCCTCACCCCGGGCAGGGGCGGCCCTCGTTGTC 780
AGGGCCTCTCCTCACTGCTGTTGTCATTGCTCCGTTTGTGTTTGTACTAATCAGTAATAA 840
AGGTTTAGAAGTTTG
```

FIG.2A

```
              10          20          30          40          50          60
              *           *           *           *           *           *
CIB    MGGSGSRLSK ELLAEYQDLT FLIKQEILLA HRRFCELLPQ EQRSVESSLR AQVPFEQILS
CALB                  GNEA SYPLEMCSHF DADEIKRLGK RFKKLDLDNS GSLSVEEFMS
CAM                                    MADQL TEEQIAEFKE AFSLFDKDGD GTITTKELTV
                                                              ────EF-1────

70          80          90          100         110         120
              *           *           *           *           *           *
CIB    LPELKANPFK ERICRVFSTS PAKDSLSFED FLDLLSVFSD TATPDIKSHY AFRIFDFDDD
CALB   LPELQQNPLV QRVIDIFDTD -GNGEVDFKE FIEGVSQFSV KGDKEQKLRF AFRIYDMDKD
CAM    MRSLGQNPEL QDMINEVDAD -GNGTIDFPE FLTMMARKMK DTDSEEEIRE AFRVFDKDGN
                                                              ────EF-1*────

130         140         150         160         170         180
              *           *           *           *           *           *
CIB    GTL-NREDLSR LVMCLTGEGE DTRLSASEMK QLIDNILEES DIDRDGTINL SEFQHVISRS
CALB   GYISNGE-LFQ -VLKMMV-GN N--LKDTQLQ QIVDKTIINA DKDGDGRISF EEFCAVVGGL
CAM    GYISAAE-L-R HMMTNL--GE K--LTDEEVD EMI-R---EA DIDGDGQVNY EEFVQMMTAK
                              ────EF-II────                    ────EF-4────

190
              *
CIB    PDFASSFKIM L
CALB   -DIHKKM-VW DV
```

FIG.2B

DNA MOLECULES ENCODING A CALCIUM-INTEGRIN BINDING PROTEIN

This invention was made with Government support under grant number 1-PO1-HL45100 from the National Institutes of Health. The government has certain rights to this invention.

FIELD OF THE INVENTION

The present invention relates to a novel $Ca^{2+}$-binding protein that interacts specifically with the integrin αIIb subunit cytoplasmic domain. This protein is expressed in platelets and interacts with the αIIb subunit of integrin αIIbβ3, to activate the fibrinogen receptor.

BACKGROUND OF THE INVENTION

Integrins are a large family of homologous transmembrane linker proteins, and are the principal receptor proteins on animal cells which bind extracellular matrix proteins such as collagen, fibronectin, and laminin. Integrins consist of two noncovalently associated transmembrane glycoprotein subunits, called α and β, both of which contribute to the binding of the target extracellular matrix protein. The binding of integrins to their ligands requires the presence of extracellular divalent cations ($Ca^{2+}$ or $Mg_{2+}$, depending on the integrin); multiple divalent-cation-binding domains are present in the large extracellular part of the α chain. Integrin receptors undergo reversible activation due to ligand binding or cellular stimulation; activation results in conformational changes in the integrin extracellular domains, reorganization of intracytoplasmic connections, and redistribution of integrins on the cell surface. (See Diamond and Springer, *Curr. Biol.* 4:506 (1994); Li et al., *J. Cell Biol.* 129:1143 (1995); Yednock et al., *j. Biol. Chem.* 270:28740 (1995)). About 20 integrin heterodimers, made from 9 types of β subunits and 14 types of α subunits have been defined.

As noted above, binding of integrins to their ligands depends on extracellular divalent cations. This property can be used to purify integrins, for example, by passing detergent-solubilized plasma membrane proteins over an affinity column containing an extra-cellular matrix protein, and then eluting the bound integrins from the column by washing in a divalent-cation-free solution. *The Molecular Biology of the Cell*, 3d ed., Alberts et al. (eds.), Garland Publishing Inc., New York, 1994, p. 996–1000.

β3 integrins are found on a variety of cells and are known to bind several matrix proteins, including fibrinogen. Blood platelets contain the αIIbβ3 fibrinogen receptor (also known as GPIIb IIIa). Platelet integrins can be activated by contact with a damaged blood vessel or by any of a number of soluble signaling molecules. Activation alters the conformation of the extracellular domain of β3 integrins, so that the extracellular domain becomes able to bind fibrinogen with high-affinity, promoting platelet aggregation and blood clot formation. In unstimulated platelets the majority of αIIbβ3 is present in an inactive conformation or low affinity state, and is unable to bind soluble ligands. Platelet agonists through their respective receptors transduce a cascade of intracellular signals ultimately leading to the conversion of αIIbβ3 into an active, high affinity state that is capable of binding soluble ligands.

Shattil et al. *J. Cell Biol.* 131:807 (1995), using the yeast two-hybrid system, recently identified a novel protein termed β3-endonexin that interacts with the cytoplasmic domain of the β3 integrin.

U.S. Pat. No. 5,523,209 to Ginsberg and O'Toole (Jun. 4, 1996) describes a method using cell culture assays to screen compounds to identify inhibitors of integrin activation.

SUMMARY OF THE INVENTION

A first aspect of the present invention is an isolated DNA molecule encoding a calcium-integrin binding protein (CIB) that binds to the integrin αIIb cytoplasmic domain, selected from the group consisting of isolated DNA of SEQ ID NO:1, isolated DNA that hybridizes to DNA of SEQ ID NO:1 under stringent conditions and which encodes a calcium-integrin binding protein that binds to the integrin αIIb cytoplasmic domain, and isolated DNA that encodes a calcium-integrin binding protein and which differs from the above DNA due to the degeneracy of the genetic code.

A second aspect of the present invention is a vector containing isolated DNA as described above.

A further aspect of the present invention is a protein encoded by DNA as described above.

A further aspect of the present invention is a protein having the amino acid sequence of SEQ ID NO:2 given herein.

A further aspect of the present invention is an aqueous preparation containing a cell membrane and calcium-integrin binding protein of SEQ ID NO:2, the cell membrane containing a functional integrin with an αIIb integrin subunit.

The foregoing and other objects and aspects of the present invention are explained in detail in the specification set forth below.

BRIEF DESCRIPTION OF THE DRAWINGS

FIG. 2A shows the cDNA (SEQ ID NO:1) and deduced amino acid sequence (SEQ ID NO:2) of clone 8, where a consensus sequence for a polyadenylation recognition site (AATAAA) is underlined; the two EF-hand motifs are boxed; putative sites of phosphorylation by protein kinase C are shown by shaded circles and casein kinase II are shown by unshaded circles; and a putative myristoylation site is shown by a square.

FIG. 2B aligns the amino acid sequence of CIB (SEQ ID NO:2) with calcineurin B (CALB) (SEQ ID NO:4) and calmodulin (CAM) (SEQ ID NO:5). Identical residues are shaded; the two EF-hand motifs of CIB are indicated by solid lines whereas the EF-hand motifs of CALB and CAM are indicated by broken lines.

DETAILED DESCRIPTION OF THE INVENTION

Figure 1A:
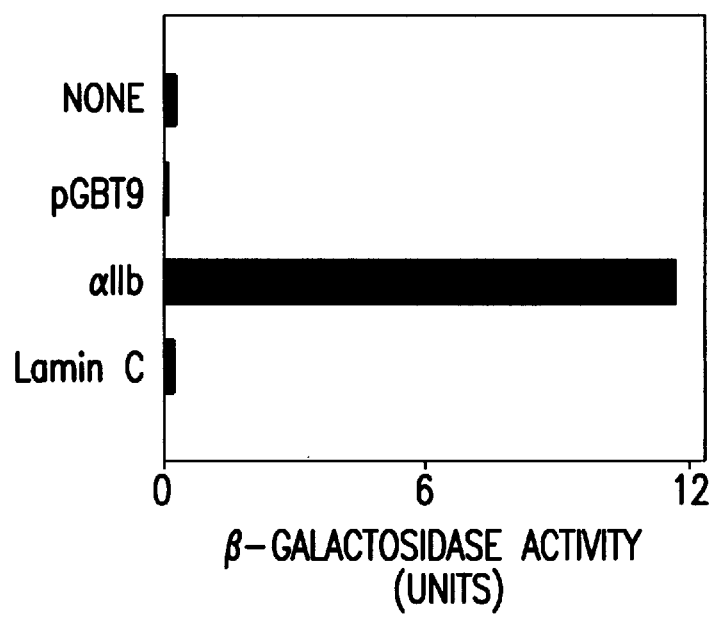
FIG. 1A is a graph showing the interaction of clone 8 protein with the αIIb cytoplasmic domain. The β-gal positive clone (clone 8) was segregated and the clone 8 plasmid DNA was isolated and transformed in yeast SFY526 either alone (None), with an empty pGBT9 vector (pGBT9); or with pGBT9 containing αIIb cytoplasmic domain cDNA (αIIb); or with pGBT9 containing lamin C, and unrelated protein cDNA (lamin C). β-gal activity in liquid medium was assayed.

The role of the αIIb and β3 cytoplasmic domains in the integrin activation process has been studied using mutants of αIIbβ3 transfected into CHO cells (Ylanne et al. *J. Cell Bio.* 122:223 (1993); Chen et al. *J. Biol. Chem.* 269:18307 (1994)). When wild type αIIbβ3 is expressed in CHO cells it is unable to bind soluble fibrinogen. However, when an (IIbβ3 construct lacking the αIIb cytoplasmic domain is expressed, the integrin becomes constitutively active and binds soluble fibrinogen with high affinity (O'Toole et al. *Science* 254:854 (1991)). Moreover, deletion of the conserved GFFKR motif of the αIIb cytoplasmic domain makes the integrin constitutively active. These data suggest that the αIIb cytoplasmic domain helps to maintain a default low-affinity state of αIIbβ3. A naturally occurring point mutation, Ser 752 to Pro in the β3 cytoplasmic domain, disrupts inside-out signaling (Chen et al. *Proc. Natl. Acad. Sci. USA* 89:10169 (1992); Chen et al. *Blood* 84:1857 (1994); O'Toole et al. *J. Cell Biol.* 124:1047 (1994)), indicating that the β3 cytoplasmic domain is involved in inducing or maintaining the high affinity state. Thus, intracellular signaling pathways probably require both integrin subunit cytoplasmic domains. It seems likely that during platelet activation, the conformations of the αIIb and β3 cytoplasmic domains are altered as a result of an interaction with cytoplasmic factors, which initiate an inside-out signal.

The mechanism by which platelets regulate the function of integrin αIIbβ3 (also termed GPIIb/IIIa), the platelet fibrinogen receptor, is postulated to involve the binding of proteins or other factors to the integrin cytoplasmic domains. To identify candidate cytoplasmic domain binding proteins, the present inventors screened a human fetal liver cDNA library in the yeast two-hybrid system, using the αIIb cytoplasmic domain as "bait", and isolated a novel 855 bp clone (SEQ ID NO: 1). The open reading frame encodes a novel 191 amino acid (21.7 kDa) polypeptide (SEQ ID NO: 2; termed CIB for calcium and integrin binding protein) specific for the cytoplasmic domain of αIIb. This protein does not interact with the αv, α2, α5, β1 or β3 integrin cytoplasmic domains. This protein has sequence similarity to two known $Ca^{2+}$ binding regulatory proteins, calcineurin B (58% similarity) and calmodulin (56% similarity), and has two EF-hand motifs corresponding to the two C-terminal $Ca^{2+}$ binding domains of these proteins. Moreover, recombinant CIB specifically binds $^{45}Ca^{2+}$ in blot overlay assays. Using RT-PCR and Western blot analysis, the present inventors detected CIB mRNA and protein respectively in human platelets. An ELISA performed using either immobilized recombinant CIB or mAb-captured αIIbβ3 indicated a specific interaction between CIB and intact αIIbβ3.

The present inventors have identified a novel $Ca^{2+}$-binding protein (CIB) that interacts specifically with the integrin αIIb subunit cytoplasmic domain, which is expressed in human platelets, and which binds to and activates the fibrinogen receptor on human platelet cells (the heterodimeric integrin αIIbβ3). The CIB protein described herein has sequence similarity to two other known $Ca^{2+}$-binding proteins, calmodulin and calcineurin B, which are involved in regulating the activity of a variety of proteins. This novel intracellular regulatory molecule is involved in the process of activation of integrin αIIbβ3, leading to platelet activation.

Integrin activation, as used herein, is defined as the process whereby the cytoplasmic domain of the integrin stimulates the ligand binding activity of the extracellular domain. With reference to the fibrinogen receptor, activation is defined as the process whereby the cytoplasmic domain of the αIIb and β3 subunits of the αIIbβ3 integrin stimulates the binding of fibrinogen to the receptor (αIIbβ3 integrin).

The full length human cDNA encoding the 21.7 kDa CIB protein which binds to the integrin αIIb cytoplasmic domain, and is expressed in platelets, has been isolated and sequenced by the present inventors (SEQ ID NO:1). The structural properties of the CIB protein indicate that it is a hydrophilic calcium binding protein, similar to calcineurin B and calmodulin. Calcineurin B is a small regulatory subunit (19 kDa) of phosphoprotein phosphatase 2B or calcineurin, the only known protein phosphatase that is regulated by $Ca^{2+}$ and calmodulin (Crabtree and Clipstone *Ann. Rev. Biochem.* 63:1045 (1994)). Calcineurin a heterodimer, also consists of a large catalytic subunit, calcineurin A. The A subunit binds calmodulin whereas the B subunit binds four atoms of $Ca^{2+}$ (Crabtree and Clipstone *Ann. Rev. Biochem.* 63:1045 (1994); Wera and Hemmings *Biochem. J.* 311:17 (1995)), and is a member of the 'EF-hand' family of $Ca^{2+}$ binding proteins. Calmodulin is a $Ca^{2+}$-dependent regulatory molecule for several different enzymes. Unlike calcineurin B and calmodulin, CIB has two rather than four EF-hand motifs.

It has been documented that a rise in intracellular $Ca^{2+}$ is a prerequisite for the activation of platelets by many agonists. It has been shown that neutrophil migration on vitronectin is regulated by calcineurin; migration is decreased by inhibitors of calcineurin or intracellular $Ca^{2+}$ chelaters, indicating that increases in $[Ca^{2+}]_i$ promote neutrophil migration and reduce integrin-mediated cell adhesion to vitronectin (Hendey et al. *Blood* 87:2038 (1996)). Interaction of fibronectin and integrin α5β1 in vitro has also been shown to be regulated by calcineurin (Pomies et al. *Biochemistry* 34:5104 (1995)).

It was further demonstrated that $Ca^{2+}$ and calcineurin regulate recycling of integrin αvβ3 to the leading edge of migrating neutrophils (Lawson and Maxfield *Nature* 376:75 (1995); Hendey et al. *Science* 258:296–299 (1992); Hendey et al. *Blood* 87:2038 (1996)). The αIIbβ3 integrin also undergoes recycling (Wencel-Drake et al. *Blood* 81:62 (1993)), in a process that downregulates platelet aggregation (Wencel-Drake et al. *Blood* 81:62 (1993); Wencel-Drake et al., *Blood* 87:602 (1996)). This event is independent of the β3 cytoplasmic domain (Ylanne et al. *J. Biol Chem.* 270:9550 (1995)), and probably dependent on the αIIb cytoplasmic domain. Barroso et al., *J. Biol. Chem.* 271:10183 (1996) have reported the cloning of a novel 22 kDa calcium binding protein that is also highly homologous to calcineurin B, and required for constitutive membrane traffic.

Both serine/threonine and tyrosine phosphorylation and dephosphorylation appear to play key roles in the regulation of integrin function (Barreuther and Grabel, *Exp. Cell Res.* 222:10 (1996)). Recently it has been shown that exposure of ligand-binding sites on αIIbβ3 correlates under some conditions with phosphorylation of the β3 subunit of αIIbβ3 (Van Willigen et al. *Biochem. J.* 314:769 (1996)). In addition, a protein kinase that interacts with the β1 and β3 cytoplasmic domains has been identified (Hannigan et al. *Nature* 379: 91 (1996)), indicating that a protein phosphatase may be directly involved in integrin regulation.

CIB was found to interact only with αIIb and not with other integrin a subunits (αv, α2, and α5), thus it is unlikely that CIB binds to the membrane proximal GFFKR region of the αIIb cytoplasmic domain, since this sequence is common to all integrin α subunits. This is in contrast to calreticulin, an intracellular $Ca^{2+}$-binding protein that binds to GFFKR (Rojiani et al. *Biochemistry* 30:9859 (1991)) and co-purified with several integrins (Leung-Hagesteijn et al. *J. Cell Sci.* 107:589 (1994)). This indicates that the CIB binding site on the αIIb cytoplasmic domain may include the highly acidic portion distal to the membrane.

The CIB proteins of the present invention may be used in methods for screening compounds for activity (agonistic or antagonistic) for integrins containing the αIIb subunit (termed "αIIb integrins" herein), or for determining the amount of integrin αIIb subunit receptor agonist or antagonist in a solution (e.g., blood plasma or serum).

A particular example is the use of the CIB proteins of the present invention to screen compounds for the ability to bind the fibrinogen receptor (αIIBβ3 integrin) and act as an agonist or antagonist for fibrinogen binding to platelet cells. For example, cells expressing the fibrinogen receptor (or transformed to express the receptor) may be lysed, and the membranes from those cells placed in an aqueous solution (containing any necessary divalent cations), which solution also contains CIB protein, to provide a preparation of activated fibrinogen receptors. A test compound is then added and any binding of the test compound to the receptor is detected. Competitive binding assays to carry out such procedures are well known in the art. Use of host cells transformed with (and expressing) DNA which encodes the fibrinogen receptor, but which cells do not ordinarily express the fibrinogen receptor, provide preparations free of possible endogenous receptors which may affect the assay. Thus, a further aspect of the present invention is an aqueous solution containing CIB and cell membranes, the cell membranes containing a functional αIIb integrin such as the αIIbβ3 fibrinogen receptor. As used herein, a membrane "containing" an integrin is a membrane containing both subunits of an integrin, arranged in the correct extracellular-transmembrane-intracellular orientation, so that the integrin is functional (able to bind appropriate ligands when activated)

A still further aspect of the present invention is an assay to screen for compounds capable of binding to the fibrinogen receptor, comprising: (a) providing an aqueous solution containing cell membranes as described above and containing CIB; (b) adding at least one test compound to the aqueous solution; and (c) washing the membrane to remove unbound test compound; (d) removing CIB from the aqueous solution to release bound compounds (for example, by washing with a solution free of CIB and free of integrins; by washing with a solution containing peptides having the sequence of the cytoplasmic domain of αIIbβ3; or by washing with a high salt solution); and (e) identifying those compounds which bound to the membrane in the presence of CIB and did not bind in the absence of CIB.

The CIB protein can also be used in methods of isolating or purifying fibrinogen. For example, a solution containing calcium, detergent-solubilized membrane fibrinogen receptor proteins and CIB protein may be combined with preparations suspected of or known to contain fibrinogen, whereupon the receptor binds to fibrinogen present. Bound fibrinogen receptors are then eluted from the column by washing (using solutions as described above) to reverse the fibrinogen-integrin binding.

The CIB protein can also be utilized in methods of isolating or purifying heterodimeric integrins containing the αIIb subunit, or isolating or purifying the αIIb subunit itself. For example, a solution containing calcium and CIB are combined with a preparation known to or suspected of containing integrins comprising the αIIb subunit or the αIIb subunit, whereupon CIB binds to αIIb subunits which are present. The CIB protein may optionally be bound to a solid substrate using techniques that are known in the art. If desired, bound integrins may then be eluted from the CIB protein by washing in a calcium-free solution.

The present calcium binding proteins may also be used in methods of isolating or removing $Ca^{2+}$ from solution, as would be apparent to one skilled in the art given the present disclosure.

The present invention also provides methods for screening compounds for the ability to inhibit, activate, or modulate the interaction of CIB and αIIb integrins, which would then affect activation of the integrin. For example, such inhibitory compounds would be useful to inhibit the activation of the fibrinogen receptor where it is desired to reduce blood coagulation for therapeutic, diagnostic, or pharmaceutical reasons. Small organic molecules are desirable candidate compounds for such screening as such molecules are often capable of passing through the plasma membrane so that they can act on integrin cytoplasmic domains. Platelet aggregation inhibitors which block the binding of fibrinogen to the extracellular domain of the fibrinogen receptor are known in the art as useful in treating vascular disorders due to platelet activation (see, e.g., U.S. Pat. No. 5,344,783 to Scarborough et al., Sep. 6, 1994).

Antibodies which specifically bind to the proteins of the present invention (i.e., antibodies which bind to a single antigenic site or epitope on the proteins) are useful for a variety of purposes. Such antibodies may be polyclonal or monoclonal in origin, but are preferably of monoclonal origin. The antibodies are preferably IgG antibodies of any suitable species, such as rat, rabbit, or horse, but are generally of mammalian origin. Fragments of IgG antibodies which retain the ability to specifically bind the proteins of the present invention, such as F(ab')$_2$, F(ab'), and Fab fragments, are intended to be encompassed by the term "antibody" herein. See generally E. Harlow and D. Lane, Antibodies: A Laboratory Manual (1988) (New York: Cold Spring Harbor Laboratory Press). The antibodies may be chimeric, as described by M. Walker et al., *Molecular Immunol.* 26, 403 (1989).

Monoclonal antibodies which bind to proteins of the present invention are made by culturing a cell or cell line capable of producing the antibody under conditions suitable for the production of the antibody (e.g., by maintaining the cell line in HAT media), and then collecting the antibody from the culture (e.g., by precipitation, ion exchange chromatography, affinity chromatography, or the like). The antibodies may be generated in a hybridoma cell line in the widely used procedure described by G. Kohler and C. Milstein, *Nature* 256, 495 (1975), or may be generated with a recombinant vector in a suitable host cell such as *Escherichia coli* in the manner described by W. Huse et al., *Science* 246, 1275 (1989).

Assays for detecting proteins of the present invention comprise the steps of, first, contacting a sample suspected of containing the proteins to antibodies capable of specifically binding the proteins, and determining the extent of binding of said antibodies to said cells. The antibody is preferably labelled, as is known in the art, to facilitate the detection of binding. Any suitable immunoassay procedure may be employed, such as radioimmunoassay, immunofluorescence, precipitation, agglutination, complement fixation, and enzyme-linked immunosorbent assay. As discussed above, while any type of antibody may be employed for the foregoing purposes, monoclonal antibodies are preferred. Those skilled in the art will be familiar with numerous specific immunoassay formats and variations thereof which may be useful for carrying out the method disclosed herein. See generally E Harlow and D. Lane, supra; E. Maggio, *Enzyme-Immunoassay*, (1980) (CRC Press, Inc., Boca Raton, Fla.); see also U.S. Pat. No. 4,727,022 to Skold et al.; U.S. Pat. No. 4,659,678 to Forrest et al., U.S. Pat. No. 4,376,110 to David et al., U.S. Pat. No. 4,275,149 to Litman et al., U.S. Pat. No. 4,233,402 to Maggio et al., and U.S. Pat. No. 4,230,767 to Boguslaski et al.

Antibodies may be conjugated to a solid support suitable for a diagnostic assay (e.g., beads, plates, slides or wells formed from materials such as latex or polystyrene) in accordance with known techniques, such as precipitation. Antibodies may likewise be conjugated to detectable labels such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., Patent In User Manual, 99–102 (November 1990) (U.S. Patent and Trademark Office).

DNAs of the present invention include those coding for proteins of SEQ ID NO:2 and those coding for proteins with extensive amino acid sequence similarity to, and having essentially the same biological properties as, the proteins disclosed herein. A particular embodiment is the DNA disclosed herein as SEQ ID NO:1 and encoding the protein given herein as SEQ ID NO:2. This definition is intended to encompass natural allelic variations therein. Thus, isolated DNA or cloned genes of the present invention can be of any species of origin, including mouse, rat, rabbit, cat, porcine, and human, but are preferably of mammalian origin. Thus, DNAs which hybridize to DNA disclosed herein as SEQ ID NO:1 (or fragments or derivatives thereof which serve as hybridization probes as discussed below) and which code for expression of a protein of the present invention (e.g., a protein according to SEQ ID NO:2) are also an aspect of this invention. Conditions which will permit other DNAs which code on expression for a protein of the present invention to hybridize to the DNA of SEQ ID NO:1 disclosed herein can be determined in accordance with known techniques. For example, hybridization of such sequences may be carried out under conditions of reduced stringency, medium stringency or even stringent conditions (e.g., conditions represented by a wash stringency of 35–40% Formamide with 5×Denhardt's solution, 0.5% SDS and 1×SSPE at 37° C.; conditions represented by a wash stringency of 40–45% Formamide with 5×Denhardt's solution, 0.5% SDS, and 1×SSPE at 42° C.; and conditions represented by a wash stringency of 50% Formamide with 5×Denhardt's solution, 0.5% SDS and 1×SSPE at 42° C., respectively) to DNA of SEQ ID NO:1 disclosed herein in a standard hybridization assay. See, e.g., J. Sambrook et al., Molecular Cloning, A Laboratory Manual (2d Ed. 1989) (Cold Spring Harbor Laboratory)). In general, sequences which code for proteins of the present invention and which hybridize to the DNA of SEQ ID NO:1 disclosed herein will be at least 75% homologous, 85% homologous, and even 95% homologous or more with SEQ ID NO:1. Further, DNAs which code for proteins of the present invention, or DNAs which hybridize to that of SEQ ID NO:1, but which differ in codon sequence from SEQ ID NO:1 due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1 (applicant specifically intends that the disclosures of all U.S. Patent references disclosed herein be incorporated herein in their entirety by reference).

The production of cloned genes, recombinant DNA, vectors, transformed host cells, proteins and protein fragments by genetic engineering is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

A vector is a replicable DNA construct. Vectors are used herein either to amplify DNA encoding the proteins of the present invention or to express the proteins of the present invention. An expression vector is a replicable DNA construct in which a DNA sequence encoding the proteins of the present invention is operably linked to suitable control sequences capable of effecting the expression of proteins of the present invention in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors comprise plasmids, viruses (e.g., adenovirus, cytomegalovirus), phage, retroviruses and integratable DNA fragments (i.e., fragments integratable into the host genome by recombination). The vector replicates and functions independently of the host genome, or may, in some instances, integrate into the genome itself.

Expression vectors should contain a promoter and RNA binding sites which are operably linked to the gene to be expressed and are operable in the host organism. DNA constructs, or "expression cassettes," of the present invention preferably include, 5' to 3' in the direction of transcription, a transcription initiation region, a structural gene (e.g., SEQ ID NO:1) positioned downstream from the transcription initiation region and operatively associated therewith, and, optionally, a termination sequence including stop signal for RNA polymerase and a polyadenylation signal for polyadenylase (e.g., the nos terminator). The promoter should be capable of operating in the cells to be transformed. The termination region may be derived from the same gene as the promoter region, or may be derived from a different gene.

DNA regions are operatively linked or operatively associated when they are functionally related to each other. For example, a promoter is operatively linked to a coding sequence if it controls the transcription of the sequence; a ribosome binding site is operatively linked to a coding sequence if it is positioned so as to permit translation. Generally, operatively linked means contiguous and, in the case of leader sequences, contiguous and in reading phase. Thus the term "operatively associated," as used herein, refers to DNA sequences on a single DNA molecule which are associated so that the function of one is affected by the other. A transcription initiation region is operatively associated with a structural gene when it is capable of affecting the expression of that structural gene (i.e., the structural gene is under the transcriptional control of the transcription initiation region). The transcription initiation region is said to be "upstream" from the structural gene, which is in turn said to be "downstream" from the transcription initiation region.

Transformed host cells are cells which have been transformed or transfected with vectors containing DNA coding for proteins of the present invention, constructed using recombinant DNA techniques. Transformed host cells ordinarily express protein, but host cells transformed for purposes of cloning or amplifying DNA coding for the proteins of the present invention need not express protein.

Suitable host cells include prokaryotes, yeast cells, or higher eukaryotic organism cells. Prokaryote host cells include gram negative or gram positive organisms, for example, *Escherichia coli* (*E. coli*) or Bacilli. Higher eukaryotic cells include established cell lines of mammalian origin as described below. Exemplary host cells are *E. coli* W3110 (ATCC 27,325), *E. coli* B, *E. coli* X1776 (ATCC 31,537), *E. coli* 294 (/ATCC 31,446). A broad variety of suitable prokaryotic and microbial vectors are available. *E. coli* is typically transformed using the plasmid pBR322. See Bolivar et al., *Gene* 2, 95 (1977). Promoters most commonly used in recombinant microbial expression vectors include the beta-lactamase (penicillinase) and lactose promoter systems (Chang et al., *Nature* 275: 615 (1978); and Goeddel et al., *Nature* 281:544 (1979)), a tryptophan (trp) promoter system (Goeddel et al., *Nucleic Acids Res.* 8:4057 (1980) and EPO App. Publ. No. 36,776) and the tac promoter (H. De Boer et al., *Proc. Natl. Acad. Sci. USA* 80:21 (1983)). The promoter and Shine-Dalgarno sequence (for prokaryotic host expression) are operably linked to the DNA of the present invention, i.e., they are positioned so as to promote transcription of the messenger RNA from the DNA.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979)), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)). While these are commonly used, other microbial promoters are suitable. Details concerning nucleotide sequences of many have been published, enabling a skilled worker to operably ligate them to DNA encoding the protein in plasmid or viral vectors (Siebenlist et al., *Cell* 20, 269 (1980)). The promoter and Shine-Dalgarno sequence (for prokaryotic host expression) are operably linked to the DNA encoding the desired protein, i.e., they are positioned so as to promote transcription of the protein messenger RNA from the DNA.

Eukaryotic microbes such as yeast cultures may be transformed with suitable protein-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the desired protein, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977)). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceral-dehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Cultures of cells derived from multicellular organisms are a desirable host for recombinant protein synthesis. In principal, any higher eukaryotic cell culture is workable, whether from vertebrate or invertebrate culture, including insect cells. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). Further, the protein promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Host cells such as insect cells (e.g., cultured *Spodoptera frugiperda* cells) and expression vectors such as the baculovirus expression vector (e.g., vectors derived from Autographa californica MNPV, Trichoplusia ni MNPV, Rachiplusia ou MNPV, or Galleria ou MNPV) may be employed to make proteins useful in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Rather than using vectors which contain viral origins of replication, one can transform mammalian cells by the method of cotransformation with a selectable marker and the chimeric protein DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

The following examples are provided to illustrate the present invention, and should not be construed as limiting thereof. In these examples, CIB means calcium-integrin binding protein; GST means glutathione S-transferase; HEL means human erythroleukemia; mAb means monoclonal antibody; PBST means phosphate buffered saline containing 0.1% Tween-20; and RT-PCR means reverse transcriptase-polymerase chain reaction.

EXAMPLE 1

Materials and Methods

Construction of Vectors: The cytoplasmic domains of integrin subunits were amplified using polymerase chain reaction (PCR) from corresponding plasmid constructs and directionally cloned into pGBT9, a yeast expression vector (Clontech, Palo Alto, Calif.) DNA sequencing of the resulting clones using automated sequencing (University of North Carolina at Chapel Hill, Automated DNA Sequencing Facility) indicated an in-frame fusion of each cytoplasmic domain to the 3' end of the Gal4 (1–147) DNA binding domain.

Two-hybrid Library Screening: Human cDNA libraries derived from fetal liver in the yeast expression vector pGAD10 were obtained from Clontech (Palo Alto, Calif.). To obtain a clone encoding a protein that interacts with the αIIb cytoplasmic domain, we used the yeast two-hybrid library screening approach developed by Fields and Song, *Nature* 340:245 (1989); Chien et al. *Proc. Natl. Acad. Sci. USA.* 88:9578 (1991)). The screening procedure used was essentially as described by the manufacturer.

Expression of GST-fusion Protein: The CIB cDNA insert was subcloned into pGEX 2T (Pharmacia, Piscataway, N.J.). The in-frame fusion was confirmed by DNA sequencing. The GST-fusion protein was purified by glutathione-Sepharose (Pharmacia, Piscataway, N.J.) affinity chromatography following elution with 10 mM reduced glutathione. Recombinant CIB was released from GST by cleavage of the GST fusion protein with 10 U of thrombin as described by the manufacturer.

$^{45}Ca^{2+}$ Binding: Proteins were separated by SDS-PAGE and electrophoretically transferred to a PVDF membrane (0.2μ pore size) following the procedure of Towbin et al. *Proc. Natl. Acad. Sci. USA* 76:4350 (1979). Blots were overlaid with $^{45}Ca^{2+}$ (1 μCi/ml) for 10 min as described by Maruyama et al. *J. Biochem.* 95:511 (1984), with or without excess unlabeled $CaCl_2$ (10 M).

RT-PCR: Total RNA was isolated from washed human platelets made free of leukocytes and other cells with TRIZOL reagent (*GIBco*BRL, Gaithersburg, Md.). The RNA was reverse transcribed using the 1st Strand cDNA Synthesis Kit (Boehinger Mannheim, Indianapolis, Ind.) and random primers. PCR amplification of specific fragments was performed for 30 cycles using specific primers. In order to amplify a 0.5 kb fragment of CIB sense 5'-CGAGTTGGCGGAGCTGT-3' (SEQ ID NO:6) and antisense 5'-AGGATGTTGTCGATGAG-3' (SEQ ID NO:7) and to amplify 1.05 kb fragment of αIIb sense 5'-GGCATTCAGTCGCTGTCA-3' (SEQ ID NO:8) and antisense 5'-CTCGTTGGCTGCGTCCA-3' (SEQ ID NO:9) primers were used.

In vitro binding assay: Microtiter wells (E.I.A./R.I.A. Plate A/2, Costar) were coated with 10 μg/ml of recombinant CIB or BSA. After blocking with 1% BSA, five-fold diluted platelet extract in 1% Triton X-100 containing 2 mM $Ca^{2+}$ was added to each well and incubated for 1 h. Wells were washed four times with PBST and the amount of integrin αIIbβ3 bound was determined using complex specific mAb 10E5 following the ELISA assay using alkaline phosphatase conjugated secondary antibody and p-nitrophenyl phosphate as substrate. Alternatively, αIIbβ3 was antibody-captured from platelet lysate following a previously described procedure (Smyth et al. *J. Biol. Chem.* 267:15568 (1992)) with modifications. Monoclonal antibody 10E5 (10 μg/ml) (developed as described above) was immobilized to microtiter wells, which were then blocked with 1% BSA, incubated with diluted platelet extract for 1 h, and washed with PBST. Recombinant CIB (10 μg/ml) in $Ca^{2+}$ containing buffer was added and the incubation was continued for 1 h. After washing, the amount of CIB bound to each well was determined using anti-CIB antiserum following the ELISA assay.

EXAMPLE 2

Isolation and Sequence Analysis of CIB cDNA

Figure 1B:
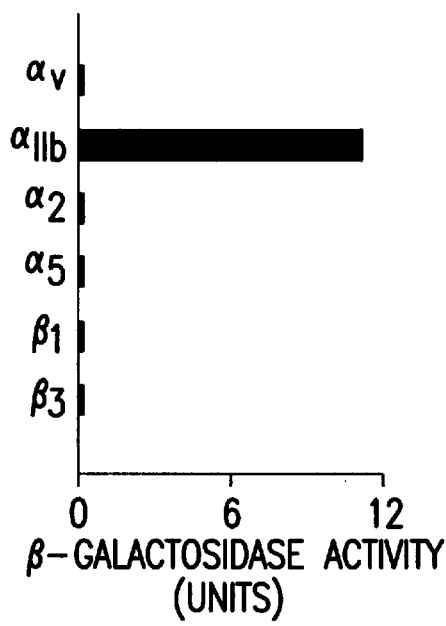
FIG. 1B is a graph showing the specificity of the interaction of the clone 8 protein with the αIIb cytoplasmic domain. Clone 8 plasmid DNA was co-transformed in yeast along with plasmids encoding various integrin cytoplasmic domains fused with the Gal4 DNA binding domain, where αv is the αv cytoplasmic domain plasmid; αIIb is the αIIb cytoplasmic domain plasmid; and β1 is the β1 cytoplasmic domain plasmid.

Using the αIIb (αIIb-cyt) cytoplasmic domain as bait, a human fetal liver cDNA library constructed in plasmid pGAD10 AND encoding the GAL4 activation domain was screened. The fetal liver produces platelets, making it a likely source of relevant platelet-related cDNA. Out of $2\times10^6$ total clones screened, a single clone was isolated (clone 8). In an experiment designed to eliminate false positives, plasmid DNA from clone 8 was isolated, purified and retransformed into the yeast SFY526 strain alone or with one of the following, (a) pGBT9, (b) a pGBT9 hybrid with an αIIb-cyt insert, or (c) a pGBT9 hybrid with the unrelated protein, lamin C. As shown in FIG. 1A, only transformants that received the αIIb-cyt hybrid and clone 8 were positive for β-galactosidase activity, indicating a true positive interaction. The clone 8 cDNA was also transformed into the yeast SFY526 strain along with plasmid pGBT9 encoding cytoplasmic domains of integrins αIIb, αv, α2, α5, β1 or β3, and β-galactosidase activity was quantified. The product of clone 8 failed to interact with the cytoplasmic domains of integrins αv, α2, α5, β1, and β3, indicating a relatively specific interaction with the αIIb cytoplasmic domain (FIG. 1B). Sequence analysis of this clone indicated an 855 bp insert (SEQ ID NO:1) and an ATG sequence (bp 47–49) in a region making it the likely translation start site (Kozak *J. Biol. Chem.* 266:19867 (1991)). The open reading frame of 573 bp (SEQ ID NO:3) encodes a polypeptide of 191 amino acids (SEQ ID NO:2) with a predicted $M_r$ of 21.7 kDa (FIG. 2A). A consensus sequence for a polyadenylation recognition site (AATAAA) is located 20 bp before the 3' end. A search of Genebank using the cDNA sequence revealed no significant similarity to any published genes. Kyte-Doolittle hydropathy analysis (Kyte and Doolittle *J. Mol. biol.* 157:105 (1982)) of the deduced amino acid sequence predicted that the protein is highly hydrophilic. CIB has a large number of acidic amino acid residues with a predicted isoelectric point of 4.48 and net charge of −13. Sequence analysis of CIB using "Prosite" revealed an N-terminal myristylation site, two consensus sites for phosphorylation by protein kinase C and five consensus sites for phosphorylation by casein kinase II (FIG. 2A). A search of protein data banks did not find the amino acid sequence of SEQ ID NO:2, but revealed that this sequence similarity shares similarity with calcineurin B, the regulatory subunit of protein phosphatase 2B (28% identity, 58% similarity), and calmodulin (27% identity, 55% similarity) (FIG. 2B). Further sequence analysis of CIB indicated the presence of two EF hand motifs that correspond to the two adjacent C-terminal $Ca^{2+}$ binding domains in calcineurin B and calmodulin. The identity between EF-hand motif I of CIB and EF-hand 3 of calcineurin B is 39% and that of EF-hand II of CIB and EF-hand 4 of calcineurin B is 35% (FIG. 2B).

EXAMPLE 3

Calcium Binding to Recombinant CIB

Figure 3A:
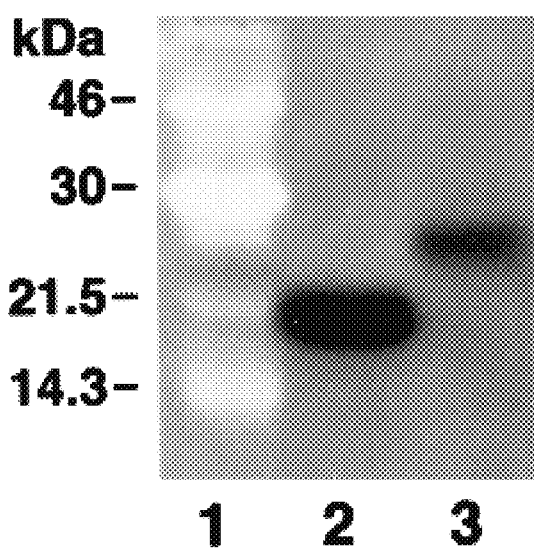
FIG. 3A is a blot overlay assay of $^{45}Ca^{2+}$ binding to CIB in the absence of 10 mM unlabeled $CaCl_2$. Proteins (2 µg each) were separated by SDS-PAGE, transferred to PVDF membranes and the membranes were overlaid with $^{45}Ca^{2+}$ (1 µCi/ml) for 10 minutes. Lane 1 contains molecular weight markers; Lane 2 contains purified bovine calmodulin; and Lane 3 contains recombinant CIB.
Figure 3B:
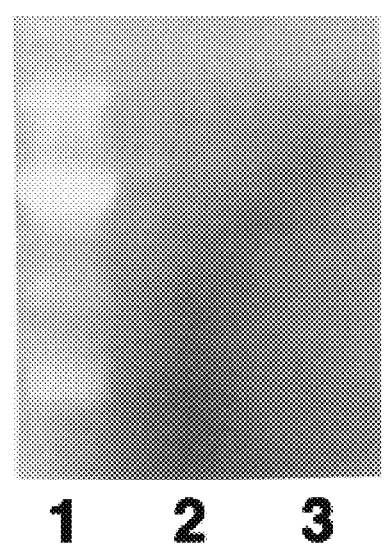
FIG. 3B is a blot overlay assay of $^{45}Ca^{2+}$ binding to CIB in the presence of 10 mM unlabeled $CaCl_2$, conducted as described for FIG. 3A. Lane 1 contains molecular weight markers; Lane 2 contains purified bovine calmodulin; and Lane 3 contains recombinant CIB.

To determine whether $Ca^{2+}$ specifically bound to CIB, $^{45}Ca^{2+}$ blot overlay assays were performed. Purified bovine calmodulin was used as a positive control. Recombinant CIB, which was purified free from GST as described in the Example 1, had a $M_r$ of 22 kDa. $^{45}Ca^{2+}$ bound to CIB and calmodulin; the binding was abolished upon inclusion of 10 mM unlabeled $Ca^{2+}$ indicating a specific interaction (FIG. 3).

EXAMPLE 4

Expression of CIB in Human Platelets

To address whether CIB is expressed in human platelets and other hematopoietic cells or cell lines, total RNA was isolated from platelets, leukocytes, HEL cells and K562 cells. RT-PCR was performed using CIB specific sense and antisense primers designed to amplify a 0.5 kb segment (SEQ ID NOS: 6 and 7). As a control for the quality of platelet RNA, αIIb specific primers, designed to amplify a 1.05 kb segment were used (SEQ ID NOs: 8 and 9). With CIB specific primers, the amplification of a 0.5 kb band from RNA derived from platelets and HEL cells was observed (FIG. 4A) indicating the presence of CIB specific mRNA. A slightly smaller sized band was observed from leukocytes and K562 cells, the identity of which is not yet known but suggestive of an alternatively spliced form of CIB mRNA. Amplification of a fragment of the expected size (~1 kb) from platelet RNA with αIIb primers served as a positive control.

Western blot analysis using two different monoclonal anti-CIB antibodies UN2 and UN7 was performed to detect CIB in platelets, HEL and K-562 cells. Both mabs detected a ~25 kDa band in the platelet but not HEL or K-562 cell extract, (FIG. 4B) despite the detection of HEL cell mRNA. The slightly higher than predicted $M_r$ observed may be due to post-translational modification.

EXAMPLE 5

In Vitro Binding of CIB to Heterodimeric Integrin αIIbβ3

Figure 4A:
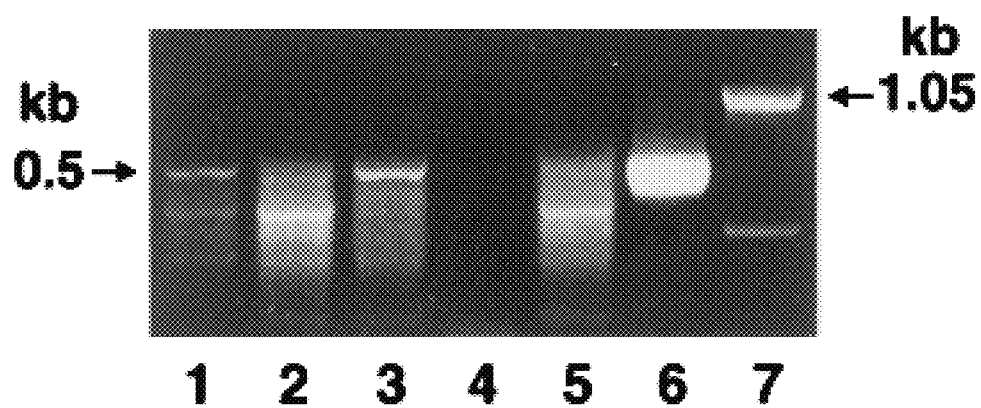
FIG. 4A is the result of RT-PCR amplification of RNA to show the expression of CIB in human platelets. Total RNAs were isolated and cDNAs were synthesized; aliquots of the cDNA synthesis reaction mixture of various RNAs were amplified for 30 cycles. Lane 1 and lane 7 contain platelet; Lane 2 contains leukocytes; Lane 3 contains HEL cells; Lane 4 contains T47D cells (a transformed breast epithelial cell line); and Lane 5 contains K562 cells. In Lane 6, clone 8 cDNA was used as a template (a positive control). Lane 1–Lane 6: CIB specific primers, 500 bp apart were used whereas in Lane 7, αIIb specific primers 1050 bp apart were used.
Figure 4B:
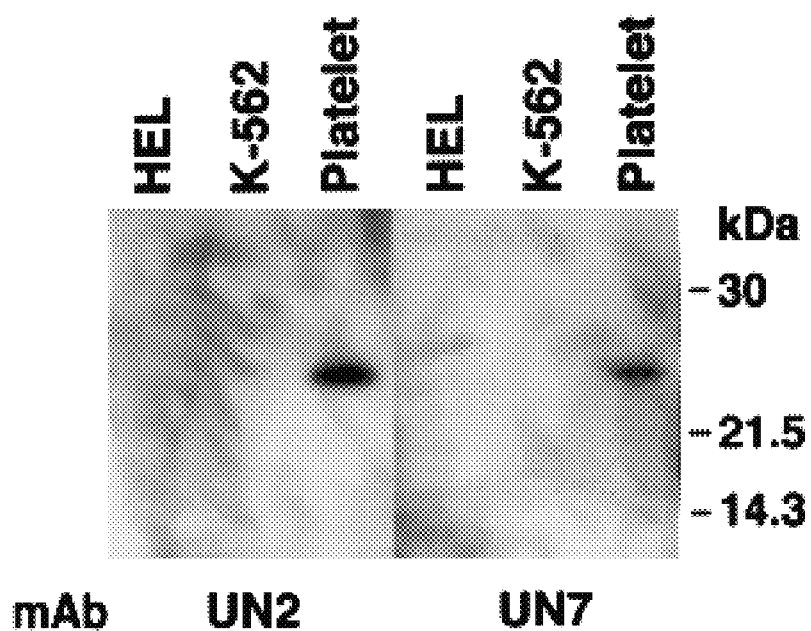
FIG. 4B is a Western blot analysis of CIB. Proteins (200 μg) from cells lysed by SDS were separated using SDS-PAGE and transferred to PVDF membranes and blotted with mAb UN2 and mAb UN7, both specific to CIB.
Figure 5A:
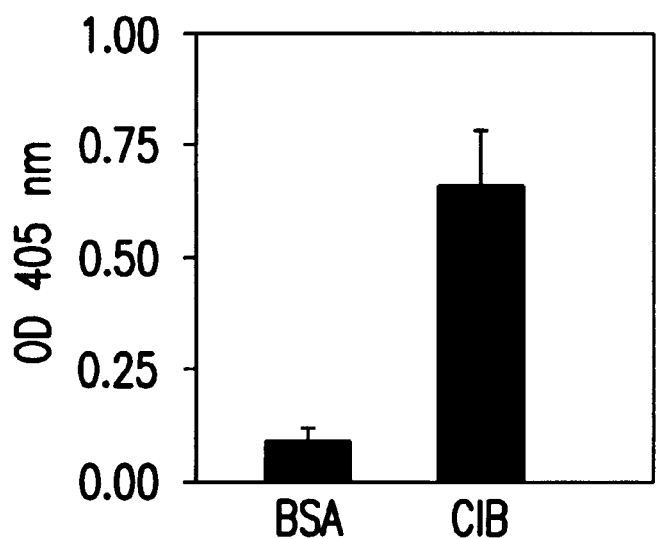
FIG. 5 shows the in vitro binding of immobilized CIB and BSA to integrin αIIbβ3, using an ELISA assay as described herein (Panel A). Panel B shows the binding of CIB to wells lacking mAB 10E5 (BSA-coated wells) and treated with platelet lysate, or to wells with immobilized 10E5 and treated with platelet lysate to capture integrin αIIbβ3. Each value shown is the mean of triplicates and representative of two separate experiments.
Figure 5B:
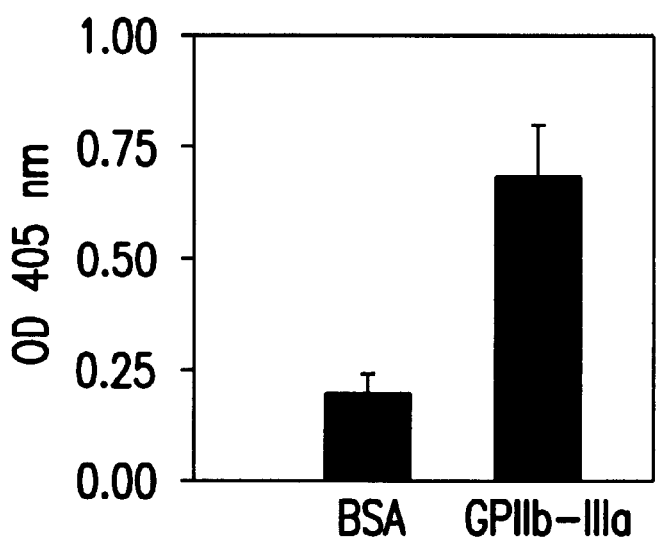

In vitro binding assays were used to determine whether CIB interacts with the intact heterodimeric αIIbβ3 integrin. In these experiments purified recombinant CIB was immobilized to microtiter wells, blocked with BSA, and αIIbβ3 from platelet extract was allowed to bind. The amount of integrin bound was quantified using mAb 10E5, a integrin complex specific antibody. Immobilized CIB bound significantly higher levels of αIIbβ3 than did immobilized BSA in the absence of CIB (FIG. 4A). Similar results were obtained in a reverse experiment in which heterodimeric integrin αIIbβ3 from platelet lysate was captured on immobilized mAb 10E5 (FIG. 4B). Significantly more recombinant CIB bound to wells containing antibody-captured integrin αIIbβ3 than to similarly treated wells lacking mAb 10E5, as detected with anti-CIB antiserum. These results demonstrate an in vitro interaction of CIB with integrin αIIbβ3.

EXAMPLE 6

Antibodies Against CIB

Polyclonal antibodies were raised against a synthetic peptide derived from the amino acid sequence (KQEILLAHRRFCELLPQEQR) (SEQ ID NO:10) of CIB that had high antigenicity, as indicated by the GCG Antigenicity Program. The antisera were analyzed by ELISA and Western blotting to determine specificity and titer for recombinant CIB. Monoclonal antibodies against CIB were developed by immunizing mice with GST-CIB and screening the culture supernatents with thrombin cleaved CIB.

EXAMPLE 7

Distribution of CIB mRNA

Using standard Northern blot techniques, the presence of CIB mRNA was studied in various human tissues. CIB mRNA was found to be highly expressed in human heart and pancreas tissue, moderately expressed in liver tissue and skeletal muscle, and expressed at low levels in brain, lung, kidney and placenta tissues.

The foregoing is illustrative of the present invention and is not to be construed as limiting thereof. The invention is defined by the following claims, with equivalents of the claims to be included therein.

---

That which is claimed is:

1. An isolated DNA molecule encoding a calcium-integrin binding protein (CIB) that binds to the integrin αIIb cytoplasmic domain, said DNA molecule selected from the group consisting of;

(a) isolated DNA having SEQ ID NO:1 and encoding a protein having SEQ ID NO:2;
   (b) isolated DNA that hybridizes to DNA of (a) above under stringent conditions, and which encodes a calcium-integri binding protein that binds to the integrin αIIb cytoplasmic domain, wherein said stringent conditions are 37° C. in a solution of 5×Denhardt's solution, 0.5% SDS, 1×SSPE, and 35% formamide;
   (c) isolated DNA that hybridizes to DNA of (a) above under stringent conditions, and which encodes a calcium-integrin binding protein that binds to the integrin αIIb cytoplasmic domain, wherein said stringent conditions are 42° C. in a solution of 5×Denhardt's solution, 0.5% SDS, 1×SSPE, and 40% formamide;
   (d) isolated DNA that hybridizes to DNA of (a) above under stringent conditions, and which encodes a calcium-integrin binding protein that binds to the integrin αIIb cytoplasmic domain, wherein said stringent conditions are 42° C. in a solution of 5×Denhardt's solution, 0.5% SDS, 1×SSPE, and 50% formamide; and
   (e) isolated DNA that encodes a calcium-integrin binding protein, and differing in nucleotide sequence from the DNA of (a) above due to the degeneracy of the genetic code.

2. A vector containing an isolated DNA molecule according to claim 1.

3. A host cell containing a vector according to claim 2.

4. A host cell according to claim 3, which cell expresses the protein encoded by said vector.

* * * * *

UNITED STATES PATENT AND TRADEMARK OFFICE
CERTIFICATE OF CORRECTION

PATENT NO.      : 6,242,587 B1
DATED           : June 5, 2001
INVENTOR(S)     : Naik et al.

It is certified that error appears in the above-identified patent and that said Letters Patent is hereby corrected as shown below:

<u>Title page,</u>
Item [75], Inventor, "Naik's" name should read -- Ulhas P. Naik --.

<u>Column 23,</u>
Line 36, should read as follows:
-- calcium-integrin binding protein that binds to the inte- --

Signed and Sealed this

Fourteenth Day of October, 2003

JAMES E. ROGAN
*Director of the United States Patent and Trademark Office*

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
       (A) LENGTH: 855 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: CDS
       (B) LOCATION: 47..619

(xi) SEQUENCE DESCRIPTION: SEQ ID NO: 1:

```
TCTGCGTCTC GAGGCGAGTT GGCGGAGCTG TGCGCGCGGC GGGGCG ATG GGG GGC           55
                                                Met Gly Gly
                                                 1

TCG GGC AGT CGC CTG TCC AAG GAG CTG CTG GCC GAG TAC CAG GAC TTG         103
Ser Gly Ser Arg Leu Ser Lys Glu Leu Leu Ala Glu Tyr Gln Asp Leu
  5              10                  15

ACG TTC CTG ACG AAG CAG GAG ATC CTC CTA GCC CAC AGG CGG TTT TGT         151
Thr Phe Leu Thr Lys Gln Glu Ile Leu Leu Ala His Arg Arg Phe Cys
 20              25                  30                  35

GAG CTG CTT CCC CAG GAG CAG CGG AGC GTG GAG TCG TCA CTT CGG GCA         199
Glu Leu Leu Pro Gln Glu Gln Arg Ser Val Glu Ser Ser Leu Arg Ala
                 40                  45                  50

CAA GTG CCC TTC GAG CAG ATT CTC AGC CTT CCA GAG CTC AAG GCC AAC         247
Gln Val Pro Phe Glu Gln Ile Leu Ser Leu Pro Glu Leu Lys Ala Asn
             55                  60                  65

CCC TTC AAG GAG CGA ATC TGC AGG GTC TTC TCC ACA TCC CCA GCC AAA         295
Pro Phe Lys Glu Arg Ile Cys Arg Val Phe Ser Thr Ser Pro Ala Lys
         70                  75                  80

GAC AGC CTT AGC TTT GAG GAC TTC CTG GAT CTC CTC AGT GTG TTC AGT         343
Asp Ser Leu Ser Phe Glu Asp Phe Leu Asp Leu Leu Ser Val Phe Ser
     85                  90                  95

GAC ACA GCC ACG CCA GAC ATC AAG TCC CAT TAT GCC TTC CGC ATC TTT         391
Asp Thr Ala Thr Pro Asp Ile Lys Ser His Tyr Ala Phe Arg Ile Phe
100                 105                 110                 115

GAC TTT GAT GAT GAC GGA ACC TTG AAC AGA GAA GAC CTG AGC CGG CTG         439
Asp Phe Asp Asp Asp Gly Thr Leu Asn Arg Glu Asp Leu Ser Arg Leu
                120                 125                 130

GTG AAC TGC CTC ACG GGA GAG GGC GAG GAC ACA CGG CTT AGT GCG TCT         487
Val Asn Cys Leu Thr Gly Glu Gly Glu Asp Thr Arg Leu Ser Ala Ser
            135                 140                 145

GAG ATG AAG CAG CTC ATC GAC AAC ATC CTG GAG GAG TCT GAC ATT GAC         535
Glu Met Lys Gln Leu Ile Asp Asn Ile Leu Glu Glu Ser Asp Ile Asp
        150                 155                 160

AGG GAT GGA ACC ATC AAC CTC TCT GAG TTC CAG CAC GTC ATC TCC CGT         583
Arg Asp Gly Thr Ile Asn Leu Ser Glu Phe Gln His Val Ile Ser Arg
        165                 170                 175

TCT CCA GAC TTT GCC AGC TCC TTT AAG ATT GTC CTG TGACAGCAGC              629
Ser Pro Asp Phe Ala Ser Ser Phe Lys Ile Val Leu
180                 185                 190
```

```
CCCAGCGTGT GTCCTGGCAC CCTGTCCAAG AACCTTTCTA CTGCTGAGCT GTGGCCAAGG      689

TCAAGCCTGT GTTGCCAGTG CGGGCCAAGC TGGCCCAGCC TGGAGCTGGC GCTGTGCAGC      749

CTCACCCCGG GCAGGGGCGG CCCTCGTTGT CAGGGCCTCT CCTCACTGCT GTTGTCATTG      809

CTCCGTTTGT GTTTGTACTA ATCAGTAATA AAGGTTTAGA AGTTTG                     855
```

(2) INFORMATION FOR SEQ ID NO: 2:

(i) SEQUENCE CHARACTERISTICS:
        (A) LENGTH: 191 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Gly Gly Ser Gly Ser Arg Leu Ser Lys Glu Leu Leu Ala Glu Tyr
 1               5                  10                  15

Gln Asp Leu Thr Phe Leu Thr Lys Gln Glu Ile Leu Leu Ala His Arg
             20                  25                  30

Arg Phe Cys Glu Leu Leu Pro Gln Glu Gln Arg Ser Val Glu Ser Ser
         35                  40                  45

Leu Arg Ala Gln Val Pro Phe Glu Gln Ile Leu Ser Leu Pro Glu Leu
     50                  55                  60

Lys Ala Asn Pro Phe Lys Glu Arg Ile Cys Arg Val Phe Ser Thr Ser
 65                  70                  75                  80

Pro Ala Lys Asp Ser Leu Ser Phe Glu Asp Phe Leu Asp Leu Leu Ser
                 85                  90                  95

Val Phe Ser Asp Thr Ala Thr Pro Asp Ile Lys Ser His Tyr Ala Phe
            100                 105                 110

Arg Ile Phe Asp Phe Asp Asp Gly Thr Leu Asn Arg Glu Asp Leu
            115                 120                 125

Ser Arg Leu Val Asn Cys Leu Thr Gly Glu Gly Glu Asp Thr Arg Leu
        130                 135                 140

Ser Ala Ser Glu Met Lys Gln Leu Ile Asp Asn Ile Leu Glu Glu Ser
145                 150                 155                 160

Asp Ile Asp Arg Asp Gly Thr Ile Asn Leu Ser Glu Phe Gln His Val
                165                 170                 175

Ile Ser Arg Ser Pro Asp Phe Ala Ser Ser Phe Lys Ile Val Leu
                180                 185                 190
```

(2) INFORMATION FOR SEQ ID NO: 3:

(i) SEQUENCE CHARACTERISTICS:
        (A) LENGTH: 573 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

```
ATGGGGGCT CGGGCAGTCG CCTGTCCAAG GAGCTGCTGG CCGAGTACCA GGACTTGACG        60

TTCCTGACGA AGCAGGAGAT CCTCCTAGCC CACAGGCGGT TTTGTGAGCT GCTTCCCCAG      120

GAGCAGCGGA GCGTGGAGTC GTCACTTCGG GCACAAGTGC CCTTCGAGCA GATTCTCAGC      180

CTTCCAGAGC TCAAGGCCAA CCCCTTCAAG GAGCGAATCT GCAGGGTCTT CTCCACATCC      240

CCAGCCAAAG ACAGCCTTAG CTTTGAGGAC TTCCTGGATC TCCTCAGTGT GTTCAGTGAC      300
```

```
ACAGCCACGC CAGACATCAA GTCCCATTAT GCCTTCCGCA TCTTTGACTT TGATGATGAC    360

GGAACCTTGA ACAGAGAAGA CCTGAGCCGG CTGGTGAACT GCCTCACGGG AGAGGGCGAG    420

GACACACGGC TTAGTGCGTC TGAGATGAAG CAGCTCATCG ACAACATCCT GGAGGAGTCT    480

GACATTGACA GGGATGGAAC CATCAACCTC TCTGAGTTCC AGCACGTCAT CTCCCTGTCT    540

CCAGACTTTG CCAGCTCCTT TAAGATTGTC CTG                                  573
```

(2) INFORMATION FOR SEQ ID NO: 4:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

```
Gly Asn Glu Ala Ser Tyr Pro Leu Glu Met Cys Ser His Phe Asp Ala
1               5                   10                  15

Asp Glu Ile Lys Arg Leu Gly Lys Arg Phe Lys Lys Leu Asp Leu Asp
            20                  25                  30

Asn Ser Gly Ser Leu Ser Val Glu Glu Phe Met Ser Leu Pro Glu Leu
        35                  40                  45

Gln Gln Asn Pro Leu Val Gln Arg Val Ile Asp Ile Phe Asp Thr Asp
50                  55                  60

Gly Asn Gly Glu Val Asp Phe Lys Glu Phe Ile Glu Gly Val Ser Gln
65                  70                  75                  80

Phe Ser Val Lys Gly Asp Lys Gly Gln Lys Leu Arg Phe Ala Phe Arg
                85                  90                  95

Ile Tyr Asp Met Asp Lys Asp Gly Tyr Ile Ser Asn Gly Glu Leu Phe
            100                 105                 110

Gln Val Leu Lys Met Met Val Gly Asn Asn Leu Lys Asp Thr Gln Leu
        115                 120                 125

Gln Gln Ile Val Asp Lys Thr Ile Ile Asn Ala Asp Lys Asp Gly Asp
    130                 135                 140

Gly Arg Ile Ser Phe Glu Glu Phe Cys Ala Val Val Gly Gly Leu Asp
145                 150                 155                 160

Ile His Lys Lys Met Val Val Asp Val
                165
```

(2) INFORMATION FOR SEQ ID NO: 5:

(i) SEQUENCE CHARACTERISTICS:
        (A) LENGTH: 145 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

```
Met Ala Asp Gln Leu Thr Glu Glu Gln Ile Ala Glu Phe Lys Glu Ala
1               5                   10                  15

Phe Ser Leu Phe Asp Lys Asp Gly Asp Gly Thr Ile Thr Thr Lys Glu
            20                  25                  30

Leu Thr Val Met Arg Ser Leu Gly Gln Asn Pro Glu Leu Gln Asp Met
        35                  40                  45
```

```
Ile Asn Glu Val Asp Ala Asp Gly Asn Gly Thr Ile Asp Phe Pro Glu
 50                  55                  60
Phe Leu Thr Met Met Ala Arg Lys Met Lys Asp Thr Asp Ser Glu Glu
 65                  70                  75                  80
Glu Ile Arg Glu Ala Phe Arg Val Phe Asp Lys Asp Gly Asn Gly Tyr
                 85                  90                  95
Ile Ser Ala Ala Glu Leu Arg His Val Met Thr Asn Leu Gly Glu Lys
            100                 105                 110
Leu Thr Asp Glu Glu Val Asp Glu Met Ile Arg Glu Ala Asp Ile Asp
        115                 120                 125
Gly Asp Gly Gln Val Asn Tyr Glu Glu Phe Val Gln Met Met Thr Ala
130                 135                 140
Lys
145
```

(2) INFORMATION FOR SEQ ID NO: 6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
       (A) DESCRIPTION: /desc = "DNA primer"

(xi) SEQUENCE DESCRIPTION: SEQ ID NO: 6:

CGAGTTGGCG GAGCTGT                                      17

(2) INFORMATION FOR SEQ ID NO: 7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
       (A) DESCRIPTION: /desc = "DNA primer"

(xi) SEQUENCE DESCRIPTION: SEQ ID NO: 7:

AGGATGTTGT CGATGAG                                      17

(2) INFORMATION FOR SEQ ID NO: 8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
       (A) DESCRIPTION: /desc = "DNA primer"

(xi) SEQUENCE DESCRIPTION: SEQ ID NO: 8:

GGCATTCAGT CGCTGTCA                                      18

(2) INFORMATION FOR SEQ ID NO: 9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear -continued

```
    (ii) MOLECULE TYPE: other nucleic acid
         (A) DESCRIPTION: /desc = "DNA primer"

(xi) SEQUENCE DESCRIPTION: SEQ ID NO: 9:

CTCGTTGGCT GCGTCCA                                                      17

(2) INFORMATION FOR SEQ ID NO: 10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Lys Gln Glu Ile Leu Leu Ala His Arg Arg Phe Cys Glu Leu Leu Pro
1               5                   10                  15

Gln Glu Gln Arg
            20
```